US012746296B2

(12) United States Patent
Delaney, Jr. et al.

(10) Patent No.: US 12,746,296 B2
(45) Date of Patent: Sep. 29, 2026

(54) IODINE LABELED HYDROGELS AND PRECURSORS THEREOF WITH IMPROVED RADIOPACITY

(71) Applicant: Boston Scientific Scimed Inc., Maple Grove, MN (US)

(72) Inventors: Joseph T. Delaney, Jr., Minneapolis, MN (US); Kolbein Kolste, Acton, MA (US); Tatyana Dyndikova, Minneapolis, MN (US); Yen-Hao Hsu, Shrewsbury, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 860 days.

(21) Appl. No.: 17/972,007

(22) Filed: Oct. 24, 2022

(65) Prior Publication Data

US 2023/0127824 A1 Apr. 27, 2023

Related U.S. Application Data

(60) Provisional application No. 63/271,297, filed on Oct. 25, 2021.

(51) Int. Cl.
*A61K 49/04* (2006.01)
*A61M 5/00* (2006.01)
*A61M 5/19* (2006.01)

(52) U.S. Cl.
CPC ......... *A61K 49/0442* (2013.01); *A61M 5/007* (2013.01); *A61M 5/19* (2013.01)

(58) Field of Classification Search
CPC .................................................. A61K 49/0442
See application file for complete search history.

(56) References Cited

U.S. PATENT DOCUMENTS

2007/0248547 A1 10/2007 Brasch et al.
2011/0142936 A1 6/2011 Campbell et al.
2021/0060183 A1 3/2021 Delaney, Jr. et al.

FOREIGN PATENT DOCUMENTS

EP 0616538 B1 4/1999
JP 07506085 A 7/1995
(Continued)

OTHER PUBLICATIONS

International Search Report and Written Opinion dated Feb. 14, 2023 for International Application No. PCT/US2022/047556.

*Primary Examiner* — Benjamin J Packard
(74) *Attorney, Agent, or Firm* — Seager, Tufte & Wickhem LLP

(57) ABSTRACT

In some embodiments, the present disclosure pertains to systems for forming a hydrogel that comprise (a) a first composition that comprises a polyiodinated polyamino compound and (b) a second composition that comprises a reactive multi-arm polymer that comprises a plurality of hydrophilic polymer arms having reactive end groups that are reactive with the amino groups of the polyiodinated polyamino compound. In some embodiments, the present disclosure pertains to medical hydrogels that are formed by reacting a polyiodinated polyamino compound and a reactive multi-arm polymer that comprises a plurality of hydrophilic polymer arms having reactive end groups that are reactive with the amino groups of the polyiodinated polyamino compound. In some embodiments, the present disclosure pertains to methods of making polyiodinated polyamino compounds.

20 Claims, 3 Drawing Sheets

(56) References Cited

FOREIGN PATENT DOCUMENTS

| | | | |
|---|---|---|---|
| WO | 9310824 | A1 | 6/1993 |
| WO | 2020155554 | A1 | 8/2020 |
| WO | 2021041230 | A1 | 3/2021 |
| WO | 2021041234 | A1 | 3/2021 |

220

112

200a

210

IODINE LABELED HYDROGELS AND PRECURSORS THEREOF WITH IMPROVED RADIOPACITY

CROSS REFERENCE TO RELATED APPLICATIONS

This application claims the benefit of U.S. Provisional Patent Application Ser. No. 63/271,297 filed on Oct. 25, 2021, the disclosure of which is incorporated herein by reference.

FIELD

The present disclosure relates to iodine labeled hydrogels, to precursors for making such hydrogels, and to methods of using such hydrogels and precursors, among other aspects. The iodine labeled hydrogels of the present disclosure are useful, for example, in various biomedical applications.

BACKGROUND

Bioerodible injectable hydrogels are a newly emerging class of materials having a variety of medical uses. As one specific example, in the case of SpaceOAR®, a long-term bioerodible injectable hydrogel based on star PEG polymers end-capped with reactive ester end groups reacting with lysine oligomers to form crosslinked hydrogels, such products are used to create or maintain space between tissues in order to reduce side effects of off-target radiation therapy. See "Augmenix Announces Positive Three-year SpaceOAR Clinical Trial Results," *Imaging Technology News*, Oct. 27, 2016.

More recently, hydrogels in which some of the star PEG branches are functionalized with 2,3,5-triiodobenzamide (TIB) groups have imparted enhanced radiopacity. As a specific example, Augmenix has developed TraceIT® Hydrogel, a bioerodible injectable hydrogel synthetic hydrogel consisting primarily of water and iodinated cross-linked star polyethylene glycol (PEG) that is visible under CT, cone beam, ultrasound and MR imaging and is useful as a tissue marker (e.g., for targeted radiation therapy). See "Augmenix Receives FDA Clearance to Market its TraceIT® Tissue Marker," *Business Wire* Jan. 28, 2013. TraceIT® hydrogel remains stable and visible in tissue for three months, long enough for radiotherapy, after which it is absorbed and cleared from the body. Id.

Although TraceIT® hydrogel is iodinated as it contains 2,3,5 triiodobenzoate groups, it is not visible on planar x-ray imaging, because the concentration of the 2,3,5 triiodobenzoate groups in the hydrogel is limited by the hydrophobicity of such groups. More generally, in hydrogels in which some of the star PEG branches are functionalized with 2,3,5-triiodobenzamide groups, an upper limit exists to how many of these groups can be added before it impacts the ability to form a smooth, consistent hydrogel. This solubility limit is in effect a limit on the amount of radiocontrast achievable with this strategy. The 2,3,5-triiodobenzamide groups need to be added to the PEG prior to reactive functionalization, adding complexity to the star-PEG manufacturing process. Furthermore, each 2,3,5-triiodobenzamide group added occupies one arm of the star polymer, reducing its capacity for crosslinking. To overcome this, lower molecular weight star PEG's can be used, but this is at the cost of a lower melting point, which can make storage and shipping a challenge. Finally, star PEG labeled with 2,3,5-triiodobenzamide end groups often show discoloration from thermal degradation. While this doesn't impact their functionality, this is a cosmetic defect that would be preferably avoided.

There is a continuing need in the biomedical arts for additional hydrogels, including radiopaque injectable hydrogels having radiopaque moieties in higher concentrations, for precursors of such hydrogels, for methods of making such hydrogels and precursors, for methods of using such hydrogels and precursors, and for systems for forming such hydrogels, among other needs.

SUMMARY

In various embodiments, the present disclosure pertains to systems for forming a hydrogel that comprise (a) a first composition that comprises a polyiodinated polyamino compound and (b) a second composition that comprises a reactive multi-arm polymer that comprises a plurality of hydrophilic polymer arms having reactive end groups that are reactive with amino groups of the polyiodinated polyamino compound.

In some embodiments, which can be used in conjunction with the preceding embodiments, the polyiodinated polyamino compound comprises a polyamino moiety comprising a plurality of amino groups and a plurality of iodinated aromatic moieties. For example, the polyamino moiety may be a residue of a lysine oligomer or a residue of a carboxy terminated polyamine, in some embodiments.

In some embodiments, which can be used in conjunction with the preceding embodiments, the iodinated aromatic moieties are 1,3-substituted-2,4,6-triiodobenzene moieties in which a substituent at each of the 1- and 3-positions comprises a hydroxyalkyl group.

In some embodiments, which can be used in conjunction with the preceding embodiments, the polyiodinated polyamino compound comprises a core, the polyamino moiety is linked to the core by an amide group, and the iodinated aromatic moieties are each linked the core by an amide group.

In some embodiments, which can be used in conjunction with the preceding embodiments, the core comprises a residue of a polycarboxylate amino compound that comprises an amino group and a plurality of carboxyl groups.

In some embodiments, which can be used in conjunction with the preceding embodiments, the hydrophilic polymer arms comprise one or more hydrophilic monomers selected from ethylene oxide, N-vinyl pyrrolidone, oxazolines, hydroxyethyl acrylate, hydroxyethyl methacrylate, PEG methyl ether acrylate, PEG methyl ether methacrylate, or PNIPAAM.

In some embodiments, which can be used in conjunction with the preceding embodiments, the reactive end groups are linked to the hydrophilic polymer arms by a hydrolysable ester.

In some embodiments, which can be used in conjunction with the preceding embodiments, the reactive end groups are electrophilic groups. In some of these embodiments, electrophilic groups are selected from imidazole esters, imidazole carboxylates, benzotriazole esters, or imide esters.

In some embodiments, which can be used in conjunction with the preceding embodiments, the hydrophilic polymer arms extend from a polyol residue.

In some embodiments, which can be used in conjunction with the preceding embodiments, the systems further comprises a delivery device.

In some embodiments, which can be used in conjunction with the preceding embodiments, the delivery device comprises a first reservoir that contains the first composition and a second reservoir that contains the second composition. During operation the first and second compositions are dispensed from the first and second reservoirs, whereupon the first and second compositions interact and crosslink with one another to form the hydrogel.

In some embodiments, which can be used in conjunction with the preceding embodiments, the first and second reservoirs comprise syringe barrels.

In some embodiments, the present disclosure pertains medical hydrogels that are formed by reacting a polyiodinated polyamino compound and a reactive multi-arm polymer that comprises a plurality of hydrophilic polymer arms having reactive end groups that are reactive with the amino groups of the polyiodinated polyamino compound.

In some embodiments, which can be used in conjunction with the preceding embodiments, the polyiodinated polyamino compound comprises a polyamino moiety comprising a plurality of amino groups and a plurality of iodinated aromatic moieties. In some of these embodiments, the polyamino moiety is a residue of a lysine oligomer or a residue of a carboxy terminated polyamine.

In some embodiments, which can be used in conjunction with the preceding embodiments, the iodinated aromatic moieties are 1,3-substituted-2,4,6-triiodobenzene moieties in which a substituent at each of the 1- and 3-positions comprises a hydroxyalkyl group.

In some embodiments, which can be used in conjunction with the preceding embodiments, the reactive end groups are linked to the hydrophilic polymer arms by a hydrolysable ester.

In some embodiments, which can be used in conjunction with the preceding embodiments, the reactive end groups are electrophilic groups selected from imidazole esters, imidazole carboxylates, benzotriazole esters, or imide esters.

In some embodiments, the present disclosure pertains to methods of making polyiodinated polyamino compounds, the methods comprising (a) forming a polyiodinated amino compound by creating amide linkages between carboxyl groups of a t-Boc protected polycarboxylate amino compound and an amino group of an iodinated amino aromatic compound, followed by deprotection of t-Boc protected amino groups; and (b) forming the polyiodinated polyamino compound by creating an amide linkage between a carboxyl group of a t-Boc protected carboxylated polyamino compound and an amino group of the polyiodinated amino compound produced in step (a), followed by deprotection of t-Boc protected amino groups.

In some embodiments, which can be used in conjunction with the preceding embodiments, the polycarboxylate amino compound is selected from 4-amino-4-(2-carboxyethyl)heptanedioic acid, N-(5-amino-1-carboxypentyl)iminodiacetic acid, L-glutamyl-L-glutamic acid, triglutamic acid and N2,N2-bis(carboxymethyl)lysine, the iodinated amino aromatic compound is 5-amino-N,N'-bis(2,3-dihydroxypropyl)-2,4,6-triiodo-1,3-benzenedicarboxamide, and the carboxylated polyamino compound is trilysine.

DETAILED DESCRIPTION

Figure 1:
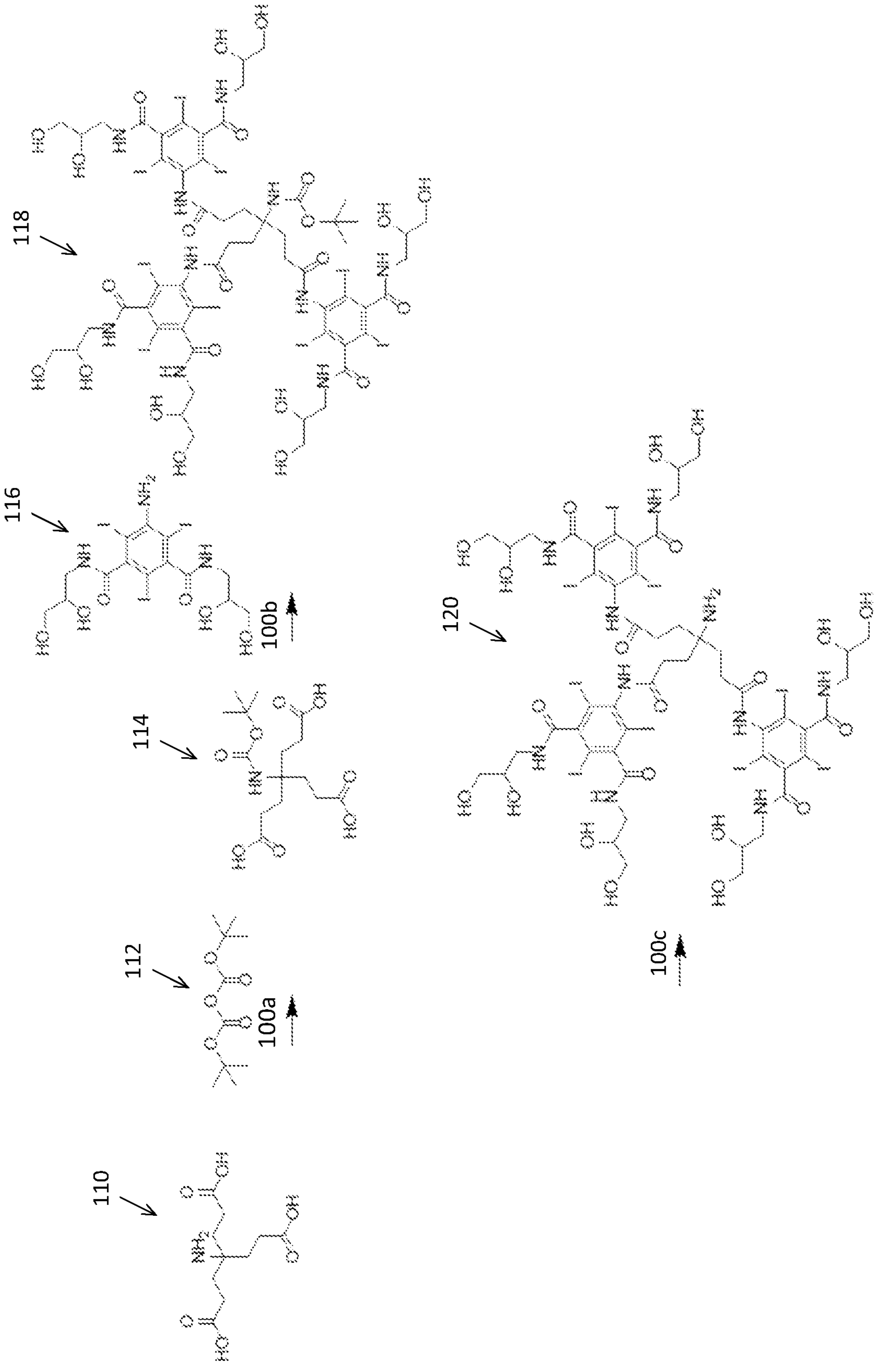
FIGS. 1, 2 and 3 are schematically illustrate a method of making a polyiodinated polyamino compound in accordance with the present disclosure.

In some aspects of the present disclosure, a radiopaque crosslinked hydrogel is provided that comprises a crosslinked reaction product of (a) a polyiodinated polyamino compound and (b) a reactive multi-arm polymer that comprises a plurality of reactive end groups that are reactive with the amino groups of the polyiodinated polyamino compound.

In some aspects of the present disclosure, a system is provided that comprises (a) a first composition that comprises a polyiodinated polyamino compound and (b) a second composition that comprises a reactive multi-arm polymer that comprises a plurality of reactive end groups that are reactive with the amino groups of the polyiodinated polyamino compound.

Such a system is advantageous, for example, in that iodine functionality, and thus radiopacity, is provided by the polyiodinated polyamino compound that acts as a crosslinker for the multi-arm polymer. This allows reactive end groups to be provided on each of the polymer arms, thereby maximizing the crosslinking capacity of the multi-arm polymer, without sacrificing radiopacity.

In some aspects, the present disclosure pertains to polyiodinated polyamino compounds which are useful, for example, as crosslinking agents.

In various embodiments, the polyiodinated polyamino compounds of the present disclosure comprise a polyamino moiety having two, three, four, five, six or more amino groups. In some embodiments, the polyiodinated polyamino compounds comprises a residue of a carboxylated polyamino compound, wherein a carboxylate group of the carboxylated polyamino compound has been reacted with an amino group to form an amide linkage to a remainder of the polyiodinated polyamino compound. Examples of carboxylated polyamino compounds may be selected from lysine oligomers such as trilysine, tetralysine, pentalysine, etc., carboxy terminated polyamines such as carboxy terminated poly(allyl amine), carboxy terminated polyvinylamine, carboxy terminated polyethyleneimine, or carboxy terminated chitosan.

In some embodiments, polyiodinated polyamino compounds comprise two, three, four, five, six or more iodinated aromatic moieties.

Examples of iodinated aromatic moieties include those that comprise a monocyclic or multicyclic aromatic structure that is substituted with (a) a plurality of iodine groups (e.g., two, three, four, five, six or more iodine groups) and (b) one or a plurality of hydrophilic functional groups (e.g., one, two, three, four, five, six or more hydrophilic functional groups).

The monocyclic or multicyclic aromatic structures may be selected, for example, from monocyclic aromatic structures such as those based on benzene and multicyclic aromatic structures such as those based on naphthalene, among others.

The hydrophilic functional groups may be selected, for example, from hydroxyalkyl groups such as $C_1$-$C_4$-hydroxyalkyl groups (e.g., $C_1$-$C_4$-monohydroxyalkyl groups, $C_1$-$C_4$-dihydroxyalkyl groups, $C_1$-$C_4$-trihydroxyalkyl groups, $C_1$-$C_4$-tetrahydroxyalkyl groups, etc.), among others. The hydroxyalkyl groups may be linked to the monocyclic or multicyclic aromatic structures directly or through any suitable linking moiety, which may be selected, for example, from amide groups, amine groups, ether groups, ester groups, or carbonate groups, among others.

In certain embodiments, the iodinated aromatic moiety may comprise a 1,3-substituted-2,4,6-triiodobenzene group, wherein a substituent at each of the 1- and 3-positions comprises a hydrophilic functional group, for example, a hydroxyalkyl group, which may be selected from those described above and which may be linked to the benzene structure directly or through any suitable linking moiety. In a particular example, the 1,3-substituted-2,4,6-triiodobenzene group may be an N,N'-bis(hydroxyalkyl)-2,4,6-triiodobenzene-1,3-dicarboxamide group, for instance, an N,N'-bis ($C_1$-$C_4$-hydroxyalky)-2,4,6-triiodobenzene-1,3-dicarboxamide group. The 1,3-substituted-2,4,6-triiodobenzene group, may in turn, be linked through the 5-position to a remainder of the polyiodinated polyamino compound through any suitable linking moiety, including an amide linkage, an amine linkage, an ester linkage, a carbonate linkage, or an ether linkage. In certain embodiments, the iodinated aromatic moiety may comprise a 1,3-($C_1$-$C_4$-hydroxyalkyl-substituted)-2,4,6-triiodobenzene group, where the hydroxyalkyl groups are linked to the benzene structure through an amide linkage, and the iodinated aromatic moiety may be linked through the 5-position to a remainder of the polyiodinated polyamino compound through an amide group.

In some embodiments, the polyiodinated polyamino compounds comprise a residue of a polyiodinated amino compound, for example, a polyiodinated aromatic amino compound that comprises a monocyclic or multicyclic aromatic structure that is substituted with a plurality of iodine groups, one or a plurality of hydrophilic functional groups such as those described above, and an amino group. For example, the polyiodinated polyamino compound may comprise a residue of such a polyiodinated amino compound, in which the amino group of the polyiodinated amino compound has been reacted with a carboxylate group to form an amide linkage to a remainder of the polyiodinated polyamino compound. In some embodiments, the polyiodinated polyamino compounds comprise a residue of a 5-amino-1,3-substituted-2,4,6-triiodobenzene compound, wherein a substituent at each of the 1- and 3-positions comprises a hydrophilic functional group, for example, a hydroxyalkyl group, which may be selected from those described above and which may be linked to the benzene structure directly or through any suitable linking moiety, and wherein the 5-amino group has been used to form an amide linkage to the remainder of the polyiodinated polyamino compound. In a particular example, the polyiodinated polyamino compound may comprise a residue of a 5-amino-1,3-hydroxyalkyl-substituted-2,4,6-triiodo-1,3-benzenedicarboxamide compound, for instance, a residue of a 5-amino-N,N'-bis(hydroxyalkyl)-2,4,6-triiodo-1,3-benzenedicarboxamide compound, such as a residue of 5-amino-N,N'-bis(2,3-dihydroxypropyl)-2,4,6-triiodo-1,3-benzenedicarboxamide, also known as 5-amino-N,N'-bis(2,3-dihydroxypropyl)-2,4,6l-triiodoisophthalamide (CAS #76801-93-9), in which the 5-amino group has been used to form an amide linkage to the remainder of the polyiodinated polyamino compound.

In some embodiments, the polyiodinated polyamino compounds comprises (a) a core, (b) a polyamino moiety attached to the core through an amide linkage, and (c) a plurality of radiopaque iodinated moieties that are attached to the core through an amide linkage.

In some embodiments, the core comprises a residue of a polycarboxylate amino compound that comprises an amino group and two, three, four, five six or more carboxyl groups. For example, the core may comprise a residue of a polycarboxylate amino compound that contains between six and twenty carbon atoms and comprises an amino group and two, three, four, five six or more carboxyl groups. In particular embodiments, the core comprises a residue of a polycarboxylate amino compound selected from 4-amino-4-(2-carboxyethyl)heptanedioic acid (CAS #176738-98-0), N-(5-amino-1-carboxypentyl)iminodiacetic acid (CAS #113231-05-3), L-glutamyl-L-glutamic acid (CAS #3929-61-1), triglutamic acid (CAS #23684-48-2), or N2,N2-bis (carboxymethyl)lysine (CAS #129179-17-5).

In some embodiments, polyiodinated polyamino compound comprises (a) a core that comprises a residue of a polycarboxylate amino compound, (b) a plurality of residues of an iodinated aromatic amino compound that comprises a monocyclic or multicyclic aromatic structure that is substituted with a plurality of iodine groups, one or a plurality of hydrophilic functional groups, and an amino group, which may be selected from those described above (e.g., a 5-amino-N,N'-bis(hydroxyalkyl)-2,4,6-triiodo-1,3-benzenedicarboxamide compound, among others), where an amino group of the iodinated aromatic amino compound has been reacted with an carboxylate group of the polycarboxylate amino compound to form a plurality of amide linkages, depending on the number of carboxylate groups, and (c) a residue of a carboxylated polyamino compound, such as those described above (e.g., selected from polylysines, carboxy terminated polyamines, etc.), where a carboxylate group of the carboxylated polyamino compound has been reacted with the amino group of the polycarboxylate amino compound to form an amide linkage to the remainder of the polyiodinated polyamino compound.

In some aspects, the present disclosure pertains to processes of making polyiodinated polyamino compounds such as those described above.

In a first process, a polyiodinated amino compound is formed by coupling (a) a polycarboxylate amino compound, in which the amino group of the polycarboxylate amino compound is protected (for example, a t-Boc-protected polycarboxylate amino compound may be formed) with (b) an iodinated amino compound to form a polyiodinated amino compound in which an amino group is protected, followed by (c) deprotection of the amino group to form the polyiodinated amino compound. Examples of polycarboxylate amino compounds are described above, with a specific example being 4-amino-4-(2-carboxyethyl)heptanedioic acid. Examples of polyiodinated amino compounds are described above with a specific example being 5-amino-N,N'-bis(2,3-dihydroxypropyl)-2,4,6-triiodoisophthalamide. With reference to FIG. 1, in a first reaction step 100*a*, the amino group of 4-amino-4-(2-carboxyethyl)heptanedioic acid (110) is protected using di-tert-butyl dicarbonate (112). The resulting t-Boc-protected tricarboxylated amino compound (114) is then coupled in a second reaction step 100*b* with 5-amino-N, N'-bis(2,3-dihydroxypropyl)-2,4,6-triiodoisophthalamide (116), yielding a t-Boc-protected polyiodinated amino compound (118). This compound (118) can be deprotected in a third reaction step 100*c*, for example, using a weak acid, yielding a polyiodinated amino compound (120). The result is a branched or arborescent structure or "active iodo-tree" that can be selectively bonded to a suitable polyamino compound.

Figure 2:
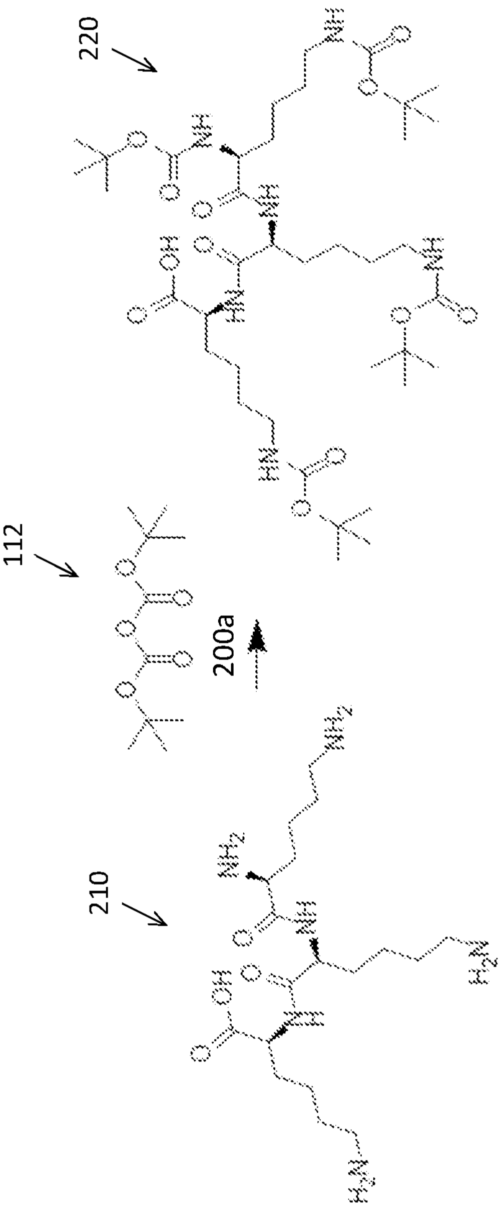

In a second process, a protected carboxylated polyamino compound in which amino groups of the carboxylated polyamino compound are protected is formed. Examples of carboxylated polyamino compound are described above and include polylysines and carboxy terminated polyamines, with a specific example being trilysine. With reference to FIG. 2, in a reaction step 200*a*, amino groups of trilysine (210) are protected using di-tert-butyl dicarbonate (112), thereby forming t-Boc-protected trilysine (220). This leaves the carboxylate group of the protected carboxylated polyamino compound (t-Boc-protected trilysine) available for amide coupling.

Figure 3:
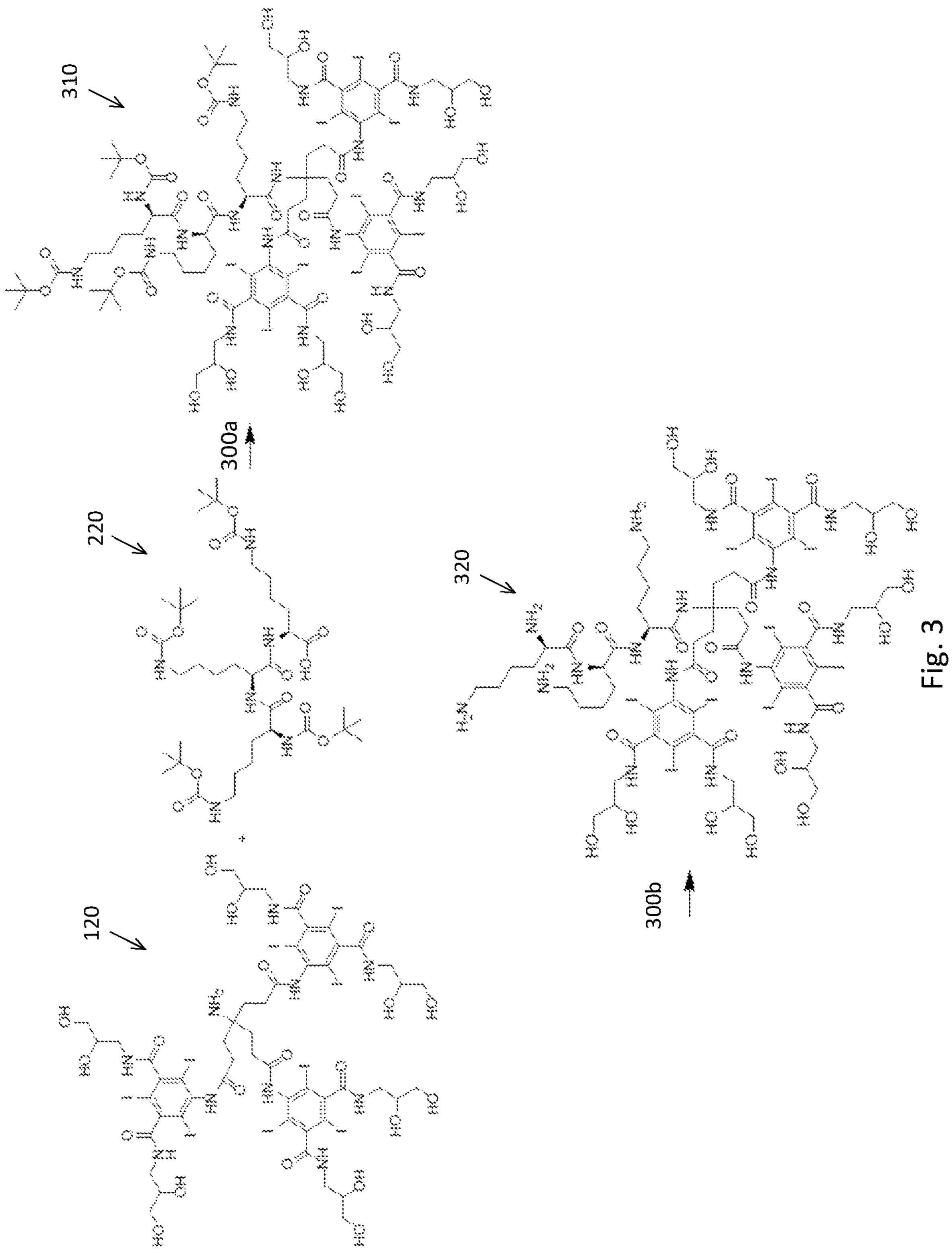

In a third process, a polyiodinated amino compound prepared as described in the first process is coupled with a protected carboxylated polyamino compound as described in the second process in an amide coupling reaction to form a protected polyiodinated polyamino compound. This is followed by deprotection, to form a final polyiodinated polyamino compound. With reference to FIG. 3, the branched or arborescent polyiodinated amino compound (120) or "active iodo-tree" of FIG. 1 is coupled to the t-Boc-protected trilysine (220) of FIG. 2 in a first reaction step 300*a* to form a protected polyiodinated polyamino compound (310). The protected polyiodinated polyamino compound (310) is then deprotected in a second reaction step 300*b* to form the final polyiodinated polyamino compound. As a result, the branched or arborescent polyiodinated amino compound of FIG. 1 is linked to trilysine, thereby forming a "trilysine-iodo-tree" that can be used to crosslink a variety of reactive multi-arm polymers as described below.

As will be appreciated by those skilled in the art, based on the polycarboxylate amino compound that is selected (see FIG. 1) and the carboxylated polyamino compound that is selected (see FIG. 2), the number of iodine groups can be varied independently of the number of amino groups in the final polyiodinated polyamino compound. More carboxylate groups in the polycarboxylate amino compound that is selected (see FIG. 1) will lead to more iodine groups relative to amino groups. Another way to increase the number of iodine groups relative to amino groups is to employ a carboxylated polyamino compound (see FIG. 2) that has two or more carboxyl groups. The carboxylated polyamino compound supplies at least one carboxylate group for coupling to the "active iodo-tree" and also provides two or more amino groups to create crosslinking functionality in the final polyiodinated polyamino compound.

As noted above, in some aspects of the present disclosure, a radiopaque crosslinked hydrogel is provided that comprises a crosslinked reaction product of (a) a polyiodinated polyamino compound such as those described above and (b) a reactive multi-arm polymer that comprises a plurality of polymer arms that have reactive end groups that are reactive with the amino groups of the polyiodinated polyamino compound. In various embodiments, such crosslinked products are visible on fluoroscopy. In various embodiments, such crosslinked products have a radiopacity for greater than 300 Hounsfield units (HU), preferably greater than 1000 HU. Such crosslinked products may be formed in vivo (e.g., using a delivery device like that described below), or such crosslinked products may be formed ex vivo and subsequently administered to a subject. Such crosslinked products can be used in a wide variety of biomedical applications, including medical devices, implants, and pharmaceutical compositions.

In various embodiments, the reactive end groups of the reactive multi-arm polymer and the amino groups of the polyiodinated polyamino compound react with one another via an amide coupling reaction. The reactive multi-arm polymer may be water soluble.

Reactive multi-arm polymers for use herein include those that comprise a plurality of polymer arms (e.g., having two, three, four, five, six, seven, eight, nine, ten, eleven, twelve or more arms), wherein two or more polymer arms of the multi-arm polymers comprise one or more reactive end groups. In some embodiments, compositions containing the reactive multi-arm polymers may be provided in which a percentage of the polymer arms comprising one or more reactive end groups may correspond to between 50% and 100% of the total number of polymer arms in the composition (e.g., ranging anywhere from 50% to 70% to 80% to 90% to 95% to 99% to 100% of the total number of polymer arms). Typical average molecular weights for the reactive multi-arm polymers for use herein range from 5 to 50 kDa. In various embodiments, the reactive multi-arm polymers for use herein have a melting point of 40° for greater, preferably 45° for greater.

In various embodiments, the polymer arms are hydrophilic polymer arms. Such hydrophilic polymer arms may be composed of any of a variety of synthetic, natural, or hybrid synthetic-natural polymers including, for example, poly(alkylene oxides) such as poly(ethylene oxide) (also referred to as polyethylene glycol or PEG), poly(propylene oxide) or poly(ethylene oxide-co-propylene oxide), poly(vinylpyrrolidone), polyoxazolines including poly(2-alkyl-2-oxazolines) such as poly(2-methyl-2-oxazoline), poly(2-ethyl-2-oxazoline) and poly(2-propyl-2-oxazoline), poly(vinyl alcohol), poly(allyl alcohol), poly(ethyleneimine), poly(allylamine), poly(vinyl amine), poly(amino acids), polysaccharides, and combinations thereof.

In some embodiments, the polymer arms extend from a core region. In certain of these embodiments, the core region comprises a residue of a polyol that is used to form the polymer arms. Illustrative polyols may be selected, for example, from straight-chained, branched and cyclic aliphatic polyols including straight-chained, branched and cyclic polyhydroxyalkanes, straight-chained, branched and cyclic polyhydroxy ethers, including polyhydroxy polyethers, straight-chained, branched and cyclic polyhydroxyalkyl ethers, including polyhydroxyalkyl polyethers, straight-chained, branched and cyclic sugars and sugar alcohols, such as glycerol, mannitol, sorbitol, inositol, xylitol, quebrachitol, threitol, arabitol, erythritol, adonitol, dulcitol, fucose, ribose, arabinose, xylose, lyxose, rhamnose, galactose, glucose, fructose, sorbose, mannose, pyranose, altrose, talose, tagatose, pyranosides, sucrose, lactose, and maltose, oligomers (defined herein as ranging from two to ten units, including dimers, trimers, tetramers, pentamers, hexamers, heptamers, octamers, enneamers and decamers) of straight-chained, branched and cyclic sugars and sugar alcohols and polymers (defined herein as eleven or more units) of straight-chained, branched and cyclic sugars and sugar alcohols, including the preceding sugars and sugar alcohols, starches, amylose, dextrins, cyclodextrins, as well as polyhydroxy crown ethers, and polyhydroxyalkyl crown ethers. Illustrative polyols also include aromatic polyols including 1,1,1-tris(4'-hydroxyphenyl) alkanes, such as 1,1,1-tris(4-hydroxyphenyl)ethane, and 2,6-bis(hydroxyalkyl)cresols, among others.

In certain beneficial embodiments, the core region comprises a residue of a polyol that contains two, three, four, five, six, seven, eight, nine, ten or more hydroxyl groups. In certain beneficial embodiments, the core region comprises a residue of a polyol that is an oligomer of a sugar alcohol such as glycerol, mannitol, sorbitol, inositol, xylitol, or erythritol, among others.

In certain embodiments, the reactive end groups may be electrophilic groups selected from imidazole esters, imidazole carboxylates, benzotriazole esters, or imide esters, including N-hydroxysuccinimidyl esters. A particularly beneficial reactive end group is an N-hydroxysuccinimidyl ester group. In certain embodiments, the reactive end groups are linked to the polymer arms via a hydrolysable ester group. For instance, the polymer arms may be terminated with the following reactive, hydrolysable groups, among others: succinimidyl glutarate groups, succinimidyl succinate groups, succinimidyl carbonate groups, or succinimidyl adipate groups, in some embodiments.

Further examples of reactive multi-arm polymers are described, for example, in U.S. Patent Application Nos. 2011/0142936, 2021/0061950, 2021/0061954 and 2021/0061957.

In some aspects of the present disclosure, a system is provided that comprises (a) a first composition that comprises a polyiodinated polyamino compound, such as is described hereinabove, and (b) a second composition that comprises a reactive multi-arm polymer such as is described hereinabove. Such systems can be used to form crosslinked hydrogels, either in vivo or ex vivo.

The first composition may be a first fluid composition comprising the polyiodinated polyamino compound or a first dry composition that comprises the polyiodinated polyamino compound, to which a suitable fluid such as water for injection, saline, etc. can be added to form a first fluid composition. In addition to the polyiodinated polyamino compound, the first composition may further comprise additional agents such as those described below.

The second composition may be a second fluid composition comprising the reactive multi-arm polymer or a second dry composition that comprises the reactive multi-arm polymer, to which a suitable fluid such as water for injection, saline, etc. can be added to form a second fluid composition). In addition to the reactive multi-arm polymer, the second composition may further comprise additional agents such as those described below.

In various embodiments, the system will include one or more delivery devices for delivering the first and second compositions to a subject. For example, the system may include a delivery device that comprises a first reservoir that contains the first composition (e.g., a first fluid composition or a first dry composition to which a suitable fluid can be added to form the first fluid composition) and a second reservoir that contains the second composition (e.g., a second fluid composition or a second dry composition to which a suitable fluid such as water for injection, saline, etc. can be added to form the second fluid composition). During operation, the first and second compositions are dispensed from the first and second reservoirs, whereupon the first and second compositions interact and crosslink with one another to form a hydrogel.

In particular embodiments, the system may include a delivery device that comprises a double-barrel syringe, which includes first barrel having a first barrel outlet, which first barrel contains the first composition, a first plunger that is movable in first barrel, a second barrel having a second barrel outlet, which second barrel contains the second composition, and a second plunger that is movable in second barrel.

In some embodiments, the device may further comprise a mixing section having a first mixing section inlet in fluid communication with the first barrel outlet, a second mixing section inlet in fluid communication with the second barrel outlet, and a mixing section outlet. In some embodiments, the device may further comprise a cannula or catheter tube that is configured to receive first and second fluid compositions from the first and second barrels. For example, a cannula or catheter tube may be configured to form a fluid connection with an outlet of a mixing section by attaching the cannula or catheter tube to an outlet of the mixing section, for example, via a suitable fluid connector such as a luer connector.

As another example, the catheter may be a multi-lumen catheter that comprise a first lumen and a second lumen, a proximal end of the first lumen configured to form a fluid connection with the first barrel outlet and a proximal end of the second lumen configured to form a fluid connection with the second barrel outlet. In some embodiments, the multi-lumen catheter may comprise a mixing section having a first mixing section inlet in fluid communication with a distal end of the first lumen, a second mixing section inlet in fluid communication with a distal end of the second lumen, and a mixing section outlet.

During operation, when the first and second plungers are depressed, the first and second fluid compositions are dispensed from the first and second barrels, whereupon the first and second fluid compositions interact and crosslink to form a hydrogel, which is administered onto or into tissue of a subject. For example, the first and second fluid compositions may pass from the first and second barrels, into the mixing section via first and second mixing section inlets, whereupon the first and second fluid compositions are mixed to form an admixture, which admixture exits the mixing section via the mixing section outlet. In some embodiments, a cannula or catheter tube is attached to the mixing section outlet, allowing the admixture to be administered to a subject after passing through the cannula or catheter tube.

As another example, the first fluid composition may pass from the first barrel outlet into a first lumen of a multi-lumen catheter and the second fluid composition may pass from the second barrel outlet into a second lumen of the multi-lumen catheter. In some embodiments the first and second fluid compositions may pass from the first and second lumen into a mixing section at a distal end of the multi-lumen catheter via first and second mixing section inlets, respectively, whereupon the first and second fluid compositions are mixed in the mixing section to form an admixture, which admixture exits the mixing section via the mixing section outlet.

In some embodiments, the first composition comprising the polyiodinated polyamino compound, the second composition comprising the reactive multi-arm polymer, or the crosslinked hydrogel product of the polyiodinated polyamino compound and the reactive multi-arm polymer may include one or more additional agents. Examples of such additional agents include therapeutic agents, and further imaging agents (beyond the iodine groups that are present in the polyiodinated polyamino compound).

Examples of further imaging agents include (a) fluorescent dyes such as fluorescein, indocyanine green, or fluorescent proteins (e.g. green, blue, cyan fluorescent proteins), (b) contrast agents for use in conjunction with magnetic resonance imaging (MRI), including contrast agents that contain elements that form paramagnetic ions, such as $Gd^{(III)}$, $Mn^{(II)}$, $Fe^{(III)}$ and compounds (including chelates) containing the same, such as gadolinium ion chelated with diethylenetriaminepentaacetic acid, (c) contrast agents for use in conjunction with ultrasound imaging, including organic and inorganic echogenic particles (i.e., particles that result in an increase in the reflected ultrasonic energy) or organic and inorganic echolucent particles (i.e., particles that result in a decrease in the reflected ultrasonic energy), (d) radiocontrast agents, such as those based on the clinically important isotope $^{99m}Tc$, as well as other gamma emitters such as $^{123}I$, $^{125}I$, $^{131}I$, $^{111}In$, $^{57}Co$, $^{153}Sm$, $^{133}Xe$, $^{51}Cr$, $^{81m}Kr$, $^{201}Tl$, $^{67}Ga$, and $^{75}Se$, among others, (e) positron emitters, such as $^{18}F$, $^{11}C$, $^{13}N$, $^{15}O$, and $^{68}Ga$, among others, may be employed to yield functionalized radiotracer coatings, and (f) contrast agents for use in connection with near-infrared (NIR) imaging, which can be selected to impart near-infrared fluorescence to the coatings of the present disclosure, allowing for deep tissue imaging and device marking, for instance, NIR-sensitive nanoparticles such as gold nanoshells, carbon nanotubes (e.g., nanotubes derivatized with hydroxyl or carboxyl groups, for instance, partially oxidized carbon nanotubes), dye-containing nanoparticles, such as dye-doped nanofibers and dye-encapsulating nanoparticles, and semiconductor quantum dots, among others. NIR-sensitive dyes include cyanine dyes, squaraines, phthalocyanines, porphyrin derivatives and boron dipyrromethane (BODIPY) analogs, among others.

Crosslinked hydrogel compositions in accordance with the present disclosure include lubricious compositions for medical applications, compositions for therapeutic agent release (e.g., by including one or more therapeutic agents in a matrix of the crosslinked hydrogel), and implants (which may be formed ex vivo or in vivo) (e.g., compositions for use as tissue markers, compositions that act as spacers to reduce side effects of off-target radiation therapy, cosmetic compositions, etc.).

What is claimed is:

1. A system for forming a hydrogel that comprises (a) a first composition that comprises a polyiodinated polyamino compound comprising (i) a polyamino moiety comprising a plurality of amino groups and (ii) a plurality of iodinated aromatic moieties and (b) a second composition that comprises a reactive multi-arm polymer that comprises a plurality of hydrophilic polymer arms having reactive end groups that are reactive with amino groups of the polyiodinated polyamino compound, wherein the polyamino moiety is a residue of a lysine oligomer or a residue of a carboxy terminated polyamine, wherein the polyiodinated polyamino compound comprises a core, wherein the polyamino moiety is linked to the core by an amide group, and wherein the iodinated aromatic moieties are each linked to the core by an amide group.

2. The system of claim 1, wherein the polyamino moiety is a residue of a lysine oligomer.

3. The system of claim 2, wherein the polyamino moiety is a trilysine residue.

4. The system of claim 1, wherein the iodinated aromatic moieties are 1,3-substituted-2,4,6-triiodobenzene moieties in which a substituent at each of the 1- and 3-positions comprises a hydroxyalkyl group.

5. The system of claim 1, wherein the iodinated aromatic moieties comprise a monocyclic or multicyclic aromatic structure that is substituted with a plurality of iodine groups and one or a plurality of $C_1$-$C_4$-hydroxyalkyl groups.

6. The system of claim 1, wherein the core comprises a residue of a polycarboxylate amino compound that comprises an amino group and a plurality of carboxyl groups.

7. The system of claim 1, wherein the hydrophilic polymer arms comprise one or more hydrophilic monomers selected from ethylene oxide, N-vinyl pyrrolidone, oxazolines, hydroxyethyl acrylate, hydroxyethyl methacrylate, PEG methyl ether acrylate or PEG methyl ether methacrylate, or PNIPAAM.

8. The system of claim 1, wherein the reactive end groups are electrophilic groups.

9. The system of claim 8, wherein the electrophilic groups are selected from imidazole esters, imidazole carboxylates, benzotriazole esters, or imide esters.

10. The system of claim 1, wherein the hydrophilic polymer arms extend from a polyol residue.

11. The system of claim 1, further comprising a delivery device.

12. The system of claim 11, wherein the delivery device comprises a first reservoir that contains the first composition and a second reservoir that contains the second composition, and wherein during operation the first and second compositions are dispensed from the first and second reservoirs, whereupon the first and second compositions interact and crosslink with one another to form the hydrogel.

13. The system of claim 11, wherein the first and second reservoirs comprise syringe barrels.

14. The system of claim 1, wherein the core comprises a residue of a polycarboxylate amino compound that comprises an amino group and two, three, four, five, or six carboxyl groups.

15. The system of claim 1, wherein the core comprises a residue of a polycarboxylate amino compound that contains between six and twenty carbon atoms and comprises an amino group and two, three, four, five, or six carboxyl groups.

16. The system of claim 1, wherein the core comprises a residue of a polycarboxylate amino compound selected from 4-amino-4-(2-carboxyethyl) heptanedioic acid, N-(5-amino-1-carboxypentyl)iminodiacetic acid, L-glutamyl-L-glutamic acid, triglutamic acid, or N2,N2-bis(carboxymethyl) lysine.

17. The system of claim 1, wherein the reactive end groups are linked to the hydrophilic polymer arms by a hydrolysable ester.

18. The system of claim 1, wherein the polymer arms comprise poly(ethylene oxide).

19. The system of claim 1, wherein the reactive end groups are imide ester groups.

20. The system of claim 19, wherein the reactive end groups are N-hydroxysuccinimidyl ester groups.

* * * * *